United States Patent [19]

Nakajima et al.

[11] Patent Number: 5,260,447

[45] Date of Patent: Nov. 9, 1993

[54] POLYHYDROXYCYCLOPENTANE DERIVATIVES, THEIR PREPARATION AND THEIR THERAPEUTIC USE

[75] Inventors: Mutsuo Nakajima; Osamu Ando; Kiyoshi Hamano; Shuji Takahashi; Takeshi Kinoshita; Hideyuki Haruyama, all of Tokyo; Akira Sato; Yasuyuki Takamatsu, both of Iwaki; Ryuzo Enokita, Tsukuba, all of Japan

[73] Assignee: Sankyo Company, Limited, Tokyo, Japan

[21] Appl. No.: 835,185

[22] Filed: Feb. 13, 1992

[51] Int. Cl.$^5$ .................. C07D 261/20; C07C 211/00
[52] U.S. Cl. .......................................... 548/222; 564/1
[58] Field of Search ............................. 548/222; 564/1

[56] References Cited

U.S. PATENT DOCUMENTS 4,138,562  2/1979  Vince ................................. 544/326

FOREIGN PATENT DOCUMENTS 0414914   3/1991  European Pat. Off. ............ 548/222
1-10010   9/1990  Japan ................................. 544/326
0667649  10/1988  Switzerland ....................... 548/222

OTHER PUBLICATIONS

Nakayama et al, "Structure of Trehalostatin: A Potent and Specific Inhibitor of Trehalase", Journal of the Chemical Society, Chemical Communications, vol. 1991, No. 14, Jul. 15, 1991, Letchworth, GB, pp. 919-921.
Gruters et al, Nature, vol. 330, pp. 74-77, Nov. 1987.
Humphries et al, Cancer Research, vol. 46, pp. 5215-5222, 1986.
Horii et al, Journal of Medicinal Chemistry, vol. 29, pp. 1038-1046, 1986.
Goda et al, Journal of Japanese Society of Food and Nutrition, vol. 34, No. 2, pp. 134-139, 1981.
Aoyagi et al, The Journal of Antibiotics, vol. XLII, No. 6, pp. 883-889, 1989.
Farr et al, Tetrahedron Letters, vol. 31, pp. 7109-7112, 1990.
Sakuda et al, Tetrahedron Letters, vol. 27, pp. 2475-2478, 1986.
Kayakiri et al, Journal of Organic Chemistry, vol. 54, pp. 4015-4016, 1989.
Morishima et al, The Journal of Antibiotics, vol. XLII, No. 6, pp. 1008-1011, 1989.
Sakuda et al, Agricultural and Biological Chemistry, vol. 51, No. 12, pp. 3251-3259, 1987.
Sakuda et al, Agricultural and Biological Chemistry, vol. 52, No. 6, pp. 1615-1617, 1988.
Nishimoto et al, The Journal of Antibiotics, vol. 44, No. 7, pp. 716-722, Jul. 1991.

Primary Examiner—Mary C. Lee
Assistant Examiner—Joseph K. McKane
Attorney, Agent, or Firm—Frishauf, Holtz, Goodman & Woodward

[57] ABSTRACT

5-Amino-1-(hydroxymethyl)cyclopentane-1,2,3,4-tetraol and 2-amino-4-(hydroxymethyl)-3a,5,6,6a-tetrahydro-4H-cyclopent[d]oxazole-4,5,6-triol, which have the ability to inhibit the activity of sugar hydrolases, especially $\beta$-glucosidase and sucrase and can thus be used for the treatment and prophylaxis of tumorous conditions, AIDS, diabetes and obesity, can be prepared by hydrolysis of trehazolin. 2-Amino-4-(hydroxymethyl)-3a,5,6,6a-tetrahydro-4H-cyclopent[d]oxazole-4,5,6-triol can also be prepared by fermentation using newly isolated strains Micromonospora sp. SANK 62390, FERM BP-3521 and Amycolatopsis sp. SANK 60791, FERM BP-3513.

2 Claims, No Drawings

POLYHYDROXYCYCLOPENTANE DERIVATIVES, THEIR PREPARATION AND THEIR THERAPEUTIC USE

BACKGROUND TO THE INVENTION

The present invention provides two novel polyhydroxycyclopentane derivatives which have certain valuable biological activities and provides methods of preparing these compounds as well as methods and compositions using them for therapeutic and prophylactic purposes.

The compounds of the present invention are 5-amino-1-(hydroxymethyl)cyclopentane-1,2,3,4-tetraol and 2-amino-4-(hydroxymethyl)-3a,5,6,6a-tetrahydro-4H-cyclopent[d]oxazole-4,5,6-triol, whose formulae (I) and (II), respectively, are given hereafter. These compounds may be prepared by fermentation or by cleavage of the compound known as trehazolin, which may be represented by the formula (III), shown below. However, 2-amino-4-(hydroxymethyl)-3a,5,6,6a-tetrahydro 4H-cyclopent[d1-oxazole-4,5,6-triol and trehazolin both undergo tautomerism, and they may, therefore, also be represented by the formulae (IIa) and (IIIa), respectively, shown below:

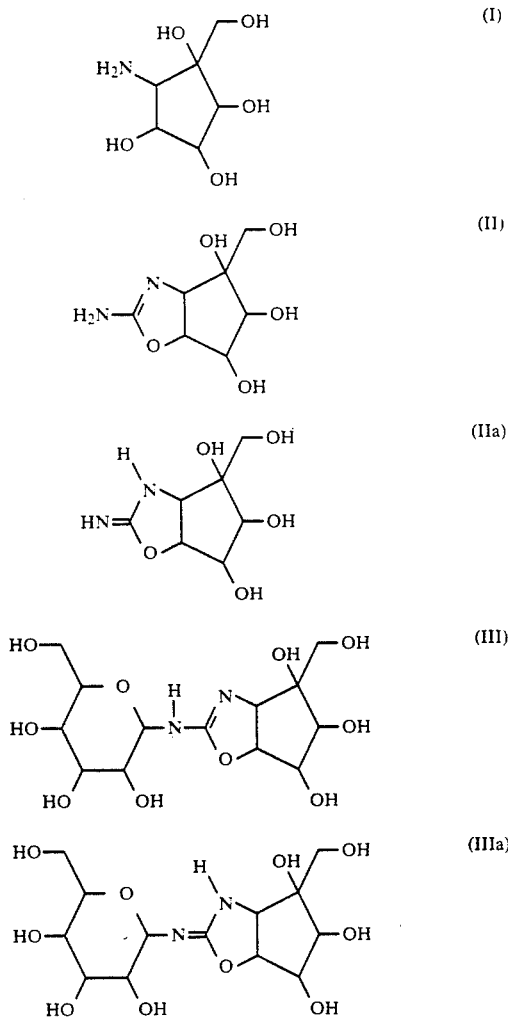

It is thought that trehazolin may be the same compound as that named "trehalostatin" in PCT International Publication No. WO 90/10010.

The compounds of the present invention have the ability to inhibit the activity of various sugar hydrolases, and, in particular, $\beta$-glucosidase and sucrase.

It has been reported that compounds having a strong inhibitory activity against $\beta$-glucosidase, such as castanospermine and deoxynojirimycin, are useful as anti-neoplastic agents and as anti-AIDS (Acquired Immune Deficiency Syndrome) agents [R. A. Gruters et al., Nature, 330, 74–77 (1987); M. J. Humphries et al., Cancer Res., 46, 5215–5222 (1986)]. It is therefore expected that compounds having the ability to inhibit the activity of $\beta$-glucosidase will be useful as anti-neoplastic or anti-AIDS agents.

It has also been reported that compounds having a strong inhibitory activity against sucrase, such as AO-128 and Acarbose, are useful as anti-diabetic agents and as anti-obesity agents [Satoshi Horii et al., Journal of Medicinal Chemistry, 29, 1038–1046 (1986); T. Goda et al., Journal of Japanese Society of Food and Nutrition, 34, (2) 134–139 (1981)]. It is therefore expected that compounds having the ability to inhibit the activity of sucrase will be useful for the treatment and prophylaxis of diabetes and obesity.

Compounds having a certain structural resemblance to the compounds of the present invention are:

the mannostatins, described, inter alia, by T. Aoyagi et al. [The Journal of Antibiotics, Vol. XLII No. 6, 883 (1989)], which are said to have the ability to inhibit the activity of $\alpha$-D-mannosidase;

(1S, 2R, 3S, 4R, 5R)-methyl[2,3,4-trihydroxy-5-(hydroxymethyl)cyclopentyl]amine, described, inter alia. by R. A. Farr et al. [Tetrahedron Letters, 31, 7109 (1990)], which is also said to have the ability to inhibit the activity of $\alpha$-mannosidase;

allosamidin, described, inter alia. by S. Sakuda et [Tetrahedron Letters, 27, 2475 (1986)], which is said to have the ability to inhibit the activity of insect chitinase; and kifunensine, described, inter alia. by H. Kayakiri et al. [J. Org. Chem., 54, 4015 (1989)], which is said to be an immunomodulator with the ability to inhibit the activity of $\alpha$-mannosidase.

BRIEF SUMMARY OF THE INVENTION

It is an object of the present invention to provide new compounds having inhibitory activity against certain sugar hydrolases.

It is a further object of the present invention to provide compounds having such activity, which are therefore expected to be useful in the treatment and prophylaxis of neoplasms, AIDS, obesity and diabetes.

Other objects and advantages will become apparent as the description proceeds.

The compounds of the present invention are 5-amino-1-(hydroxymethyl)cyclopentane-1,2,3,4-tetraol, which has the formula (I), given above, and 2-amino-4-(hydroxymethyl)-3a,5,6,6a-tetrahydro-4H-cyclopent[d]oxazole-4,5,6-triol, which has the formula (II), given above.

The invention also provides a pharmaceutical composition comprising an effective amount of 5-amino-1-(hydroxymethyl)cyclopentane-1,2,3,4-tetraol in admixture with a pharmaceutically acceptable carrier, diluent or excipient.

The invention also provides a pharmaceutical composition comprising an effective amount of 2-amino-4-(hydroxymethyl)-3a,5,6,6a-tetrahydro-4H-cyclopent[d]oxazole-4,5,6-triol in admixture with a pharmaceutically acceptable carrier, diluent or excipient.

The invention still further provides a method for the treatment or prophylaxis of tumors or of pre-tumorous conditions in an animal, e.g. a mammal, especially a human being, by the administration thereto of an effective dose of 5-amino-1-(hydroxymethyl)-cyclopentane-1,2,3,4-tetraol.

The invention still further provides a method for the treatment or prophylaxis of acquired immune deficiency syndrome in an animal, e.g. a mammal, especially a human being, by the administration thereto of an effective dose of 5-amino-1-(hydroxymethyl)-cyclopentane-1,2,3,4-tetraol.

The invention still further provides a method for the treatment or prophylaxis of diabetes or obesity in an animal, e.g. a mammal, especially a human being, by the administration thereto of an effective dose of 2-amino-4-(hydroxymethyl)-3a,5,6,6a-tetrahydro-4H-cyclopent[d]-oxazole-4,5,6-triol.

DETAILED DESCRIPTION OF INVENTION

5-Amino-1-(hydroxymethyl)cyclopentane-1,2,3,4-tetraol may be prepared by the hydrolysis of trehazolin or of 2-amino-4 (hydroxymethyl)-3a,5,6,6a-tetrahydro-4H-cyclopent[d]oxazole-4,5,6-triol, as described in greater detail hereafter. 2-Amino-4-(hydroxymethyl)-3a,5,6,6a-tetrahydro-4H-cyclopent[d]oxazole-4,5,6-triol may be prepared by the hydrolysis of trehazolin or by fermentation using a microorganism of the genus Micromonospora or Amycolatopsis.

Trehazolin, which may be used as a starting material for preparing the compounds of the present invention, may be prepared by cultivation of a trehazolin-producing microorganism of the genus Micromonospora or Amycolatopsis, preferably a trehazolin-producing microorganism of the genus Micromonospora.

An example of a trehazolin-producing microorganism of the genus Micromonospora is Micromonospora sp. SANK 62390. This microorganism was first deposited at the domestic depository of the Fermentation Research Institute, Agency of Industrial Science and Technology, Tsukuba-shi, Ibaraki.ken, Japan, on 26th Jul., 1990 under the accession number FERM P-11631, and was then deposited under the terms of the Budapest Treaty at the Fermentation Research Institute, Agency of Industrial Science and Technology, on 21st Aug. 1991 with the accession no. FERM BP-3521.

An example of a trehazolin-producing microorganism of the genus Amycolatopsis is Amycolatopsis sp. SANK 60791, which was deposited under the terms of the Budapest Treaty at the Fermentation Research Institute, Agency of Industrial Science and Technology, Tsukuba-shi, Ibaraki-ken, Japan, on 14th Aug. 1991 with the accession no. FERM BP-3153.

Both of these are newly isolated strains and both form part of the present invention.

CHARACTERISATION OF MICROORGANISMS

Micromonospora sp. SANK 62390

The strain Micromonospora sp. SANK 62390 has the following mycological properties.

1. Morphological characteristics

Strain SANK 62390 grows normally or slightly poorly during cultivation at 28° C. for a period of 7 to 14 days on a conventional agar culture medium used for strain identification. Substrate hyphae elongate properly and branch with a light orange, orange to dark brownish gray color, but without the incisions or sharp turns observed in strains of the genus Nocardia. Aerial mycelia are rudimentary and are colored white to brownish white. Spores are observed on substrate hyphae alone and form one by one on a relatively short sporangiophore. The spore shape is spherical and the spore surface is smooth. No special organs, such as sporangia, sclerotia, whirls or the like, are observed.

2. Growth on various media

The strain was cultivated at 28° C. for 14 days on various culture media and exhibited the properties shown in Table 1. Expression of the color tones is indicated by the color tip number in "Guide to Color Standard" edited by the Japan Color Research Institute.

In the Table, the following abbreviations are used:
G: Growth; AM: Aerial mycelium; R: Reverse; SP: Soluble pigment

TABLE 1

| Properties of strain SANK 62390 | | |
|---|---|---|
| Medium | Characteristic | Properties |
| Sucrose-nitrate agar | G: | slightly poor, smooth, light orange (3-9-6) |
| | AM: | not formed |
| | R: | light orange (3-9-6) |
| | SP: | not produced |
| Glucose-asparagine agar | G: | slightly poor, smooth, yellowish orange (12-7-7) |
| | AM: | not formed |
| | R: | light orange (6-8-7) |
| | SP: | not produced |
| Glycerol-asparagine agar (ISP 5) | G: | slightly poor, smooth, light orange (8-7-6) |
| | AM: | not formed |
| | R: | light brownish gray (2-6-6) |
| | SP: | not produced |
| Inorganic salts-starch agar (ISP 4) | G: | good, smooth, light orange (8-7-6) |
| | AM: | not formed |
| | R: | gray (N-5) |
| | SP: | not produced |
| Tyrosine agar (ISP 7) | G: | slightly poor, smooth, dull orange (6-8-6) |
| | AM: | barely formed, rudimentary, white |
| | R: | brownish white (2-9-7) |
| | SP: | not produced |
| Nutrient agar (DIFCO) | G: | slightly poor, smooth, yellow orange (10-8-7) |
| | AM: | not formed |
| | R: | dull yellowish orange (8-8-7) |
| | SP: | not produced |
| Yeast extract-malt extract agar (ISP 2) | G: | good, smooth, dark brownish gray (1-4-6) |
| | AM: | barely formed, rudimentary, brownish white (1-8-6) |
| | R: | brownish black (1-2-6) |
| | SP: | not produced |
| Oatmeal agar (ISP 3) | G: | good, smooth, orange (10-7-6) |
| | AM: | barely formed, rudimentary, white |
| | R: | orange (12-7-6) |
| | SP: | not produced |
| Water agar | G: | slightly poor, smooth, pale yellowish orange (2-9-9) |
| | AM: | not formed |
| | R: | gray (N-5) |
| | SP: | not produced |
| Potato extract-carrot extract agar | G: | good, smooth, yellowish gray (1-9-10) |
| | AM: | barely formed, rudimentary, white |

TABLE 1-continued

| Medium | Characteristic | Properties of strain SANK 62390 Properties |
|---|---|---|
| | R: | brownish white (2-9-7) |
| | SP: | not produced |

3. Physiological properties

The physiological properties of strain SANK 62390 observed over the period of from day 2 to day 21 after the beginning of cultivation at 28° C. are shown in Table 2.

TABLE 2

| | |
|---|---|
| Hydrolysis of starch | positive |
| Liquefaction of gelatin | positive |
| Reduction of nitrate | negative |
| Coagulation of milk | positive |
| Peptonization of milk | positive |
| Production of melanoid pigments | |
| (Medium 1)* | negative |
| (Medium 2)* | negative |
| (Medium 3)* | negative |
| Decomposition of substrate | |
| Casein | positive |
| Tyrosine | negative |
| Xanthine | negative |
| Temperature range for growth (Medium 4)* | 17–42° C. |
| Optimum temperature for growth (Medium 4)* | 27–32° C. |
| Salt toleration | 2% |

*Medium 1: Tryptone-yeast extract broth (ISP 1)
Medium 2: Peptone-yeast extract-iron agar (ISP 6)
Medium 3: Tyrosine agar (ISP 7)
Medium 4: Yeast extract-malt extract agar (ISP 2)

Strain SANK 62390 was also cultivated at 28° C. using Pridham-Gottlieb agar (ISP 9) as the cultivation medium. The assimilation of carbon sources observed after cultivation for 14 days is shown in Table 3.

TABLE 3

| | |
|---|---|
| D-Glucose | utilized |
| D-Fructose | utilized |
| L-Arabinose | utilized |
| L-Rhamnose | not utilized |
| D-Xylose | utilized |
| Sucrose | not utilized |
| Inositol | utilized |
| Raffinose | utilized |
| D-Mannitol | not utilized |
| Control | not utilized |

4. Cell components

The cell walls of strain SANK 62390 were analyzed by the method of B. Becker et al. [Applied Microbiology, 12, 421 –423 (1984)] and were found to include meso-diaminopimelic acid. Furthermore, the sugar components of the whole cell walls of strain SANK 62390 were analyzed by the method of M. P. Lechevalier [Journal of Laboratory & Clinical Medicine, 71, 934 (1968)] and were found to include arabinose and xylose but not mycolic acid. The acyl-type peptide glycan in the cell wall was shown to be of the glycolyl type. The major menaquinone components detected were MK-10($H_6$), MK-10($H_4$) and MK-10($H_8$).

It is therefore evident that this microorganism should be classified as a new strain, belonging to the genus Micromonospora of the family Actinomycetes. On this basis, it was designated as Micromonospora sp. SANK 62390.

Amycolatopsis sp. SANK 60791

The strain Amycolatopsis sp. SANK 60791 has the following mycological properties:

1. Morphological characteristics

Strain SANK 60791 grows normally or slightly poorly during cultivation at 28° C. for a period of from 7 to 14 days on a conventional agar culture medium used for strain identification. Substrate hyphae elongate properly and branch smoothly or irregularly with a brownish white, pale yellowish brown to dim yellow color. Aerial mycelia are few or rudimentary with a white, pale yellow to light orange color. At later stages of the incubation, substrate hyphae and aerial mycelia divided in sections and aerial mycelia having a bacillus structure are sometimes observed. The hyphae elongate without the sharp turns observed in strains of the genus Nocardia. No special organs, such as sporangia, sclerotia, whirls or the like, are observed.

2. Growth on various media

The strain was cultivated at 28° C. for 14 days on various culture media and exhibited the properties shown in Table 4. Expression of the color tones is indicated by the color tip number in "Guide to Color Standard" edited by the Japan Color Research Institute.

In the Table, the following abbreviations are used:
G: Growth; AM: Aerial mycelium; R: Reverse; SP: Soluble pigment

TABLE 4

| Medium | Characteristic | Properties of strain SANK 60791 Properties |
|---|---|---|
| Sucrose-nitrate agar | G: | good, smooth, yellowish gray (1-9-10) |
| | AM: | slightly poor, white |
| | R: | yellowish gray (2-9-10) |
| | SP: | not produced |
| Glucose-asparagine agar | G: | slightly poor, smooth, light orange (3-9-6) |
| | AM: | barely formed, yellowish gray (2-9-10) |
| | R: | light brown (3-8-6) |
| | SP: | not produced |
| Glycerin-asparagine agar (ISP 5) | G: | good, smooth, brownish white (2-9-7) |
| | AM: | rudimentary, white |
| | R: | pale yellowish brown (6-8-8) |
| | SP: | not produced |
| Inorganic salts-starch agar (ISP 4) | G: | slightly poor, smooth, pale yellowish brown (4-8-9) |
| | AM: | rudimentary, pale yellow (3-9-10) |
| | R: | pale yellowish brown (6-8-9) |
| | SP: | not produced |
| Tyrosine agar (ISP 7) | G: | very good, wrinkled, brownish white (2-9-6) |
| | AM: | barely formed, light orange (3-9-6) |
| | R: | light orange (6-8-7) |
| | SP: | not produced |
| Nutrient agar (DIFCO) | G: | good, smooth, pale yellowish brown (4-8-8) |
| | AM: | rudimentary, white |
| | R: | pale yellow (3-9-8) |
| | SP: | not produced |
| Yeast extract-malt extract agar (ISP 2) | G: | good, wrinkled, dull yellow (10-7-9) |
| | AM: | rudimentary, white |
| | R: | dull yellowish orange (10-7-8) |
| | SP: | not produced |
| Oatmeal agar (ISP 3) | G: | slightly poor, smooth, pale yellowish brown (4-8-9) |
| | AM: | rudimentary, white |
| | R: | pale yellow (4-9-9) |

TABLE 4-continued

Properties of strain SANK 60791

| Medium | Characteristic | Properties |
| --- | --- | --- |
| | SP: | not produced |
| Water agar | G: | slightly poor, smooth, yellowish gray (1-9-10) |
| | AM: | slightly poor, white |
| | R: | yellowish gray (1-9-10) |
| | SP: | not produced |
| Potato extract-carrot extract agar | G: | slightly poor, smooth, yellowish gray (1-9-10) |
| | AM: | rudimentary, white |
| | R: | yellowish gray (2-9-11) |
| | SP: | not produced |

3. Physiological properties

The physiological properties of strain SANK 60791 observed over the period of from day 2 to day 21 after the beginning of cultivation at 28° C. are shown in Table 5.

TABLE 5

| | |
| --- | --- |
| Hydrolysis of starch | negative |
| Liquefaction of gelatin | positive |
| Reduction of nitrate | positive |
| Coagulation of milk | positive |
| Peptonization of milk | negative |
| Production of melanoid pigment | |
| (Medium 1)* | negative |
| (Medium 2)* | negative |
| (Medium 3)* | negative |
| Decomposition of substrate | |
| Casein | negative |
| Tyrosine | positive |
| Xanthine | negative |
| Salt toleration (Medium 4)* | 3% |

*Medium 1: Tryptone-yeast extract broth (ISP 1)
Medium 2: Peptone-yeast extract-iron agar (ISP 6)
Medium 3: Tyrosine agar (ISP 7)
Medium 4: Yeast extract-malt extract agar (ISP 2)

The strain SANK 60791 was also cultivated at 28° C. using Pridham-Gottlieb agar (ISP 9) as the cultivation medium. The assimilation of carbon sources observed after cultivation for 14 days is shown in Table 6.

TABLE 6

| | |
| --- | --- |
| D-Glucose | utilized |
| D-Fructose | utilized |
| L-Arabinose | slightly utilized |
| L-Rhamnose | utilized |
| D-Xylose | utilized |
| Sucrose | utilized |
| Inositol | not utilized |
| Raffinose | utilized |
| D-Mannitol | utilized |
| Control | not utilized |

4. Cell components

The cell walls of strain SANK 60791 were analyzed by the method of B. Becker et al. [Applied Microbiology, 12, 421–423 (1984)] and were found to include meso-diaminopimelic acid. Furthermore, the sugar components of the whole cell walls of strain SANK 60791 were analyzed by the method of M. P. Lechevalier Journal of Laboratory & Clinical Medicine, 71, 934 (1968)] and were found to include arabinose but not mycolic acid. The acyl-type peptide glycan in the cell wall was proved to be of the acetyl type. The major menaquinone component detected was MK-9($H_4$).

It is therefore reasonable that the microorganism should be classified as a new strain, belonging to the genus Amycolatopsis of the family Actinomycetes. On this basis, it was designated as Amycolatopsis sp. SANK 60791.

Identification of strains SANK 62390 and SANK 60791 was made according to the standards of the ISP (The International Streptomyces Project), Bergey's Manual of Systematic Bacteriology, Vol. 4, The Actinomycetes, Vol. 2 and other recent literature on the Actinomycetes.

It has been established that the strains SANK 62390 and SANK 60791 produce trehazolin and 2-amino-4-(hydroxymethyl)-3a,5,6,6a-tetrahydro-4H-cyclopent[d]oxazole-4,5,6-triol. However, as is well known, the properties of fungi in general, and actinomycetous microorganisms in particular, can vary considerably and such fungi can readily undergo mutation, both through natural causes and as the result of induction by artificial means (for example, ultraviolet irradiation, radioactive irradiation, chemical treatment, etc.). Accordingly, the present invention embraces the use of any microorganism which can be classified within the genus Micromonospora or Amycolatopsis and which shares with strains SANK 62390 and SANK 60791 the characteristic ability to produce trehazolin and 2-amino-4-(hydroxymethyl)-3a,5,6,6a-tetrahydro-4H-cyclopent[d]oxazole-4,5,6-triol. The new microorganisms, strains SANK 62390 and SANK 60791, are not expected to be an exceptional, and the terms "SANK 62390" and "SANK 60791" all mutants of these strains which share with strains SANK 62390 and SANK 60791 the characteristic ability to produce trehazolin and 2-amino-4-(hydroxymethyl)-3a,5,6,6a-tetrahydro-4H-cyclopent[d]oxazole-4,5,6-triol. Moreover, these mutants include those obtained by means of genetic engineering techniques, for example, recombination, transduction, transformation or the like. It is a matter of simple experimentation to determine, on the basis of the information given herein regarding the properties of trehazolin and 2-amino-4-(hydroxymethyl) 3a,5,6,6a-tetrahydro-4H-cyclopent[d]-oxazole-4,5,6-triol, whether any given strain produces these compounds or produces them in sufficient quantity to render that strain of potential commercial interest.

The trehazolin and 2-amino-4-(hydroxymethyl) 3a,5,6,6a-tetrahydro-4H-cyclopent[d]oxazole-4,5,6-triol in accordance with the present invention may be prepared by the culture of these strains of fungus in culture media of the type conventionally used for the production of other fermentation products from similar microorganisms. Such media necessarily contain microbiologically assimilable sources of carbon and of nitrogen as well as inorganic salts, as is well known to those skilled in the art.

Preferred examples of carbon sources include: glucose, fructose, maltose, sucrose, mannitol, glycerol, dextrin, oat, rye, corn starch, potato starch, corn flour, soybean meal, cottonseed cake, cottonseed oil, molasses, citric acid, tartaric acid and the like. Such compounds can be used alone or in any suitable combination. In general the amount used may vary in the range of from 1 to 10% by weight of the culture medium.

Preferred nitrogen sources are normally protein-containing materials such as are commonly used in a fermentation process. Examples of such nitrogen sources include: soybean meal, wheat bran, peanut meal, cottonseed cake, cottonseed oil, cottonseed meal, casein hydrolyzates, pharmamin, fish meal, corn steep liquor, peptone, meat extract, yeast, yeast extract, malt extract, sodium nitrate, ammonium nitrate, ammonium sulfate and the like. These nitrogen sources may be used alone or in any suitable combination. In general, we prefer to employ them at a concentration between 0.2 and 6% by weight of the culture medium.

The nutritive inorganic salts that may be incorporated into the culture medium are conventional salts that are capable of providing various ions necessary to the growth of microorganisms, such as sodium, ammonium, calcium, phosphate, sulfate, chloride and carbonate ions. In addition, the medium should contain minor amounts of essential trace elements, such as potassium, calcium, cobalt, manganese, iron and magnesium.

When the process of the present invention is carried out by a liquid culture technique, an antifoaming agent, such as a silicone oil, plant oil or surface-active agent, is preferably used in the culture medium. The pH of the culture medium for producing trehazolin or 2-amino-4 (hydroxymethyl) 3a,5,6,6a-tetrahydro-4H-cyclopent[d]oxazole-4,5,6-triol by the cultivation of microorganisms of the genera Micromonospora and Amycolatopsis, especially strains SANK 62390 and SANK 60791, preferably varies within the range of from 5.0 to 8.0, more preferably from 6.5 to 7.5.

The cultivation may be carried out at any temperature within the range of from 15° to 38° C., although a temperature of from 22° to 38° C. is preferred for good growth, and a temperature of from 22° to 28° C. is preferred in order to optimise the production of trehazolin and 2-amino-4 (hydroxymethyl)-3a,5,6,6a-tetrahydro-4H-cyclopent[d]oxazole-4,5,6-triol.

These compounds are produced under aerobic culture conditions and conventional aerobic culture methods, such as solid culture, shaking culture and aeration-stirring (submerged) culture methods, may be used. In the case of small scale cultivation, shaking culture for a few days at 28° C. is typical. In such a small scale culture method, the culture may be initiated with 1 or 2 proliferation steps, producing seed cultures in, for example, Erlenmeyer flasks, fitted with baffle plates, which serve as a liquid flow regulator. The medium for the seed culture steps preferably contains both carbon and nitrogen sources. In the preferred sequence of operations for such small scale cultivation, the seed culture flasks are shaken in a constant temperature incubator at 28° C. for 7 days or until sufficient growth is achieved. The grown seed culture is then transferred to a second seed medium or to the production medium. When an intermediate growth phase is used, essentially the same method is used for growth and an aliquot of the resulting intermediate product is inoculated into the production medium. The inoculated flask may be incubated for several days whilst shaking, and, after completion of the incubation, the contents of the flask may be centrifuged or filtered.

In the case of large scale production, the use of an appropriate fermentor equipped with a stirrer and an aeration apparatus is preferred. In this case, the nutritive medium can be prepared inside the fermentor. The medium is preferably sterilized by elevating the temperature to 125° C.; after cooling, the sterilized medium may be inoculated with the previously prepared seed culture. The culture then proceeds under stirring and aeration at, for example, 28° C. This method is suitable for obtaining the compounds of the present invention in a large amount.

The progress of the cultivation and the amount of the desired trehazolin and 2-amino-4-(hydroxymethyl)-3a,5,6,6a-tetrahydro-4H-cyclopent[d]oxazole-4,5,6-triol produced as the culture proceeds can be determined by measuring the biological activities of the compounds or by high performance liquid chromatography or gas chromatography/mass spectrometry of a purified sample of compound from the culture broth, as described in more detail hereafter. Trehazolin has an inhibitory activity against silkworm trehalase, and its production may be monitored by following the activity of the culture broth against silkworm trehalase, using techniques such as that illustrated in the following Test Example 3.

On the other hand, the production of 2-amino-4-(hydroxymethyl)-3a,5,6,6a-tetrahydro-4H-cyclopent[d]oxazole-4,5,6-triol is best monitored by high performance liquid chromatography or gas chromatography/mass spectrometry. This may be carried out by contacting the culture broth with a suitable adsorbent resin [e.g. that sold under the trade name Amberlite IRC-50 ($NH_4^+$)] to adsorb the 2-amino-4-(hydroxymethyl)-3a,5,6,6a-tetrahydro-4H-cyclopent[d]oxazole-4,5,6-triol, e.g. in a chromatography column. This may be followed by: washing with water; eluting with a suitable eluent, e.g. a 0.5N aqueous solution of ammonia; concentrating the eluate, e.g. by evaporation under reduced pressure; and lyophilizing the residue, to produce a powder. The amount of the 2-amino-4-(hydroxymethyl)-3a,5,6,6a-tetrahydro-4H-cyclopent[d]oxazole-4,5,6-triol in the powder may be measured using high performance liquid chromatography. Alternatively, the compound may first be acetylated, and the amount of the 2-amino-4-(hydroxymethyl)-3a,5,6,6a-tetrahydro-4H-cyclopent[d]oxazole-4,5,6-triol in the powder may be measured using gas chromatography/mass spectrometry.

Generally, the amount of trehazolin reaches a maximum between 72 and 150 hours after initiation of the fermentation, whilst the amount of 2-amino-4-(hydroxymethyl)-3a,5,6,6a-tetrahydro-4H-cyclopent[d]oxazole. 4,5,6-triol reaches a maximum between 96 and 168 hours after initiation of the fermentation. However, the exact time will vary depending upon the temperature and other fermentation conditions, and the exact optimum time for any set of conditions can easily be determined by following the production of the desired compound, as suggested above.

When using a strain of the genus Micromonspora, both trehazolin and 2-amino-4-(hydroxymethyl)-3a,5,6,-,6a-tetrahydro-4H-cyclopent[d]oxazole-4,5,6-triol are normally produced, and these may be separated by conventional means during the recovery procedure, as described below. Strains of the genus Amycolatopsis normally only produce 2-amino-4-(hydroxymethyl)-3a,5,6,6a-tetrahydro-4H-cyclopent[d]oxazole 4,5,6-triol. Both compounds are released into the liquid phase, although they are both also present in the mycelium. They are most easily recovered from the liquid phase.

After completion of the cultivation, the desired trehazolin and/or 2-amino-4-(hydroxymethyl)-3a,5,6,-,6a-tetrahydro-4H-cyclopent[d]oxazole-4,5,6-triol, which are present in the liquid phase of the culture broth, can be fractionated by filtering off the mycelium and other solid materials, preferably using diatomaceous earth as a filter aid, or by centrifugation. These compounds, which are then present in the filtrate or in the supernatant can be recovered by extraction and can then be purified by conventional means, making use of their physico-chemical properties.

For example, these compounds can be recovered from the filtrate or the supernatant by passing it through a column containing an adsorbent, such as an ion exchange resin, for example Amberlite IRC-50 or CG-50, or Dowex 50WX4 or SBR-P, so that either the impurities are retained by the resin and thus removed, or the desired compound is retained and then recovered by elution, for example with aqueous ammonia. Examples of other adsorbents include activated charcoal or other adsorbent resins, such as Amberlite XAD-2 or XAD-4 (a product of Rohm and Haas Co.), or Diaion HP-10, HP-20, CHP-20, HP-50 (a product of Mitsubishi Kasei Corporation). A solution containing the trehazoline and/or 2-amino-4-(hydroxymethyl)-3a,5,6,6a-tetrahydro-4H-cyclopent[d]oxazole-4,5,6-triol is passed through an adsorbent layer containing one of these other adsorbents, as described above, so that either the impurities are retained by the adsorbent and thus removed, or the desired compound is retained and then recovered by elution, for example with aqueous methanol, aqueous acetone or the like.

The trehazolin or 2-amino-4-(hydroxymethyl)-3a,5,6,6a-tetrahydro-4H-cyclopent[d]oxazole-4,5,6-triol thus obtained can further be purified by various known techniques, for example: absorption column chromatography using a carrier, such as silica gel or Florisil; partition column chromatography using Avicel (a product of Asahi Chemical Industry Co., Ltd.) or Sephadex LH-20 (a product of Pharmacia Inc.); or high performance liquid chromatography using a normal, reverse phase or ion exchange column.

The 5-amino-1-(hydroxymethyl)cyclopentane-1,2,3,4-tetraol, compound (I) of the present invention, and 2-amino-4-(hydroxymethyl)-3a,5,6,6a-tetrahydro-4H-cyclopent[d]oxazole-4,5,6-triol, compound (II) of the present invention, can be prepared by hydrolysis of the trehazolin prepared as described above.

This reaction is preferably effected in the presence of an acid and must be carried out in the presence of water. There is no particular limitation on the nature of the acid to be employed, and any acid commonly used for conventional hydrolysis reactions may equally be employed here. Examples include such inorganic acids as hydrochloric acid or sulfuric acid and such organic acids as acetic acid or propionic acid, in an aqueous solution. A preferred acid is hydrochloric acid.

The reaction can take place over a wide range of temperatures, and the precise reaction temperature is not critical to the invention. In general, we find it convenient to carry out the reaction at a temperature of from about room temperature to 120° C., more preferably from 90° C. to 100° C. The time required for the reaction may also vary widely, depending on many factors, notably the reaction temperature and the nature of the reagents and solvent employed, and, as explained below, on the desired product.

It will be appreciated that both 5-amino-1-(hydroxymethyl)cyclopentane-1,2,3,4 tetraol and 2-amino-4-(hydroxymethyl)-3a,5,6,6a-tetrahydro-4H-cyclopent[d]-oxazole-4,5,6-triol are prepared from the same starting material, using the same hydrolysis reaction. Accordingly, in general, the product will contain a mixture of the two compounds. However, it is possible to favor the production of one of these compounds over the other by appropriate selection of reaction conditions. Thus, generally milder conditions will favor the production of 2-amino-4-(hydroxymethyl)-3a,5,6,6a-tetrahydro-4H-cyclopent[d]oxazole-4,5,6-triol, whilst more rigorous conditions will favor the production of 5-amino-1-(hydroxymethyl)cyclopentane-1,2,3,4-tetraol.

Accordingly, for the production of 2-amino-4-(hydroxymethyl)-3a,5,6,6a-tetrahydro-4H-cyclopent[d]oxazole-4,5,6-triol, we prefer to employ a relatively milder acidic reagent, for example 0.2N aqueous hydrochloric acid, and the reaction is preferably allowed to continue for a period of from 1 hour to 2 days, more preferably from 5 to 6 hours.

On the other hand, to encourage the reaction to go all the way to produce 5-amino-1-(hydroxymethyl)cyclopentane-1,2,3,4-tetraol, a stronger acid, such as 4N aqueous hydrochloric acid, is preferred, and the reaction is preferably allowed to continue for a period of from 1 hour to 2 days, more preferably from 20 hours to 24 hours.

Additionally, 5-amino-1-(hydroxymethyl)cyclopentane-1,2,3,4-tetraol may be prepared by the hydrolysis of 2-amino-4-(hydroxymethyl)-3a,5,6,6a-tetrahydro-4H-cyclopent[d]oxazole-4,5,6-triol. In this case, the hydrolysis reaction of the present invention may be carried out in the presence of an acid or of a base. There is no particular limitation upon the nature of the acid or base used, and any acid or base conventionally used in hydrolysis reactions may equally be used here.

Where an acid is used for the reaction, examples of suitable acids include: inorganic acids, such as the hydrohalic acids (for example hydrochloric acid, hydrobromic acid or hydroiodic acid), sulfuric acid, perchloric acid, phosphoric acid and nitric acid; organic carboxylic acids, such as lower alkanoic acids (for example formic acid, acetic acid, oxalic acid or trifluoroacetic acid); lower alkanesulfonic acids (for example methanesulfonic acid, ethanesulfonic acid or trifluoromethanesulfonic acid); and arylsulfonic acids (for example benzenesulfonic acid or p-toluenesulfonic acid etc.). The preferred acids are the inorganic acids, particularly hydrochloric acid.

In general, the reaction is preferably carried out in the presence of a solvent. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol or butanol; sulfoxides, such as dimethyl sulfoxide or sulfolane; organic acids, especially fatty acids, such as acetic acid or propionic acid; and water. Preferred solvents include water and a mixtures of water and an organic solvent.

The amount of acid used is normally and preferably from 1 to 20 moles, more preferably from 5 to 10 moles, per mole of the starting compound.

The reaction can take place over a wide range of temperatures, and the precise reaction temperature is not critical to the invention. In general, we find it convenient to carry out the reaction at a temperature of from about room temperature to 150° C., more preferably 90° C. to 110° C. The time required for the reaction may also vary widely, depending on many factors, notably the reaction temperature and the nature of the reagents and solvent employed. However, provided that the reaction is effected under the preferred conditions outlined above, a period of from 1 hour to 2 days, more preferably from 20 hours to 30 hours will usually suffice.

Where a base is used for the reaction, examples of suitable bases include: inorganic bases, such as alkali metal hydroxides (for example lithium hydroxide, sodium hydroxide or potassium hydroxide); alkaline earth metal hydroxides (for example calcium hydroxide or barium hydroxide); alkali metal carbonates (for example sodium carbonate or potassium carbonate); and alkali metal halides (for example sodium iodide, sodium bromide or potassium iodide); and organic bases, such as ammonia; alkylamines (for example triethylamine); and heterocyclic amines (for example morpholine, N-ethylpiperidine or pyridine).

In general, the reaction is preferably carried out in the presence of a solvent. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol or butanol; ethers, such as tetrahydrofuran or dioxane; sulfoxides, such as dimethyl sulfoxide or sulfolane; and water. Preferred solvents include water and mixtures of water and an organic solvent.

The amount of added base is normally and preferably from 0.01 to 10 moles, more preferably from 1 to 5 moles, per mole of the starting compound.

The reaction can take place over a wide range of temperatures, and the precise reaction temperature is not critical to the invention. In general, we find it convenient to carry out the reaction at a temperature of from 0° C. to 120° C., more preferably from about room temperature to 100° C. The time required for the reaction may also vary widely, depending on many factors, notably the reaction temperature and the nature of the reagents and solvent employed. However, provided that the reaction is effected under the preferred conditions outlined above, a period of from 0.5 hour to 2 days, more preferably from 1 hour to 20 hours will usually suffice.

The desired compounds of formulae (I) and (II) can be recovered from the reaction mixture by conventional means commony used for the separation and recovery of an organic compound, for example, the various chromatography techniques, notably column chromatography or preparative thin layer chromatography. Various options have been described in connection with the separation and purification of trehazolin and 2-amino-4-(hydroxymethyl)-3a,5,6,6a-tetrahydro-4H-cyclopent[d]-oxazole-4,5,6-triol when prepared by fermentation, and these options may also be employed to separate and purify the 5-amino-1-(hydroxymethyl)cyclopentane-1,2,3,4-tetraol and 2-amino-4-(hydroxymethyl)-3a,5,6,6a-tetrahydro-4H-cyclopent[d]oxazole-4,5,6-triol obtained as described above by hydrolysis.

The compounds of the present invention, 5-amino-1-(hydroxymethyl)cyclopentane-1,2,3,4-tetraol and 2-amino-4-(hydroxymethyl)-3a,5,6,6a-tetrahydro-4H-cyclopent[d]oxazole-4,5,6-triol, each contains at least one basic nitrogen atom, and can thus form acid addition salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such acid addition salts include: salts with mineral acids, especially hydrohalic acids (such as hydrofluoric acid, hydrobromic acid, hydroiodic acid or hydrochloric acid), perchloric acid, nitric acid, carbonic acid, sulfuric acid or phosphoric acid; salts with lower alkylsulfonic acids, such as methanesulfonic acid, trifluoromethane sulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

5-Amino-1-(hydroxymethyl)cyclopentane-1,2,3,4-tetraol has the ability to inhibit the activity of $\beta$-glucosidase and has a low toxicity, and can therefore be expected to be useful in the treatment and prophylaxis of tumors and AIDS. 2-Amino-4-(hydroxymethyl)-3a,5,6,6a-tetrahydro-4H-cyclopent[d]oxazole-4,5,6-triol has the ability to inhibit the activity of sucrase and has a low toxicity, and can therefore be expected to be useful in the treatment and prophylaxis of diabetes and obesity.

When these compounds are intended for therapeutic use, they may be administered alone or in a suitable pharmaceutical formulation containing, in addition to the active compound one or more conventional diluents, carriers or excipients. The nature of the formulation will, of course, depend on the intended route of administration. However, for the oral route, the compound is preferably formulated as powders, granules, tablets or capsules. For parenteral administration, it is preferably formulated as an injection. These preparations can be prepared according to the known means by addition of such additives as vehicles, binders, disintegrators, lubricants, stabilizers and corrigents. Although the dosage may vary depending upon the symptoms and age of the patient, the nature and severity of the disease or disorder and the route and manner of administration, in the case of oral administration to an adult human patient, the compounds of the present invention may normally be administered at a daily dose of from. 1 to 1000 mg. The compounds may be administered in a single dose, or in divided doses, for example two or three times a day.

The preparation of the compounds of the present invention is further illustrated by the following non-limiting Examples.

EXAMPLE 1

Preparation of Trehazolin

1(A) Cultivation

A loopful of Micromonospora sp. SANK 62390 was used to inoculate each of three 500 ml Erlenmeyer flasks all fitted with baffle plates and each containing 80 ml of Medium 1 (having the composition specified below), and the inoculated flasks were incubated at 28° C.

for 216 hours on a rotary shaking machine rotating at a speed of rpm, to give a first seed culture.

| Medium 1: | |
|---|---|
| Glucose | 1% |
| Glycerine | 1% |
| Oatmeal | 0.5% |
| Sucrose | 1% |
| Soybean meal | 2% |
| Casamino acids | 0.5% |
| Pressed yeast | 1% |
| $CaCO_3$ | 0.1% |
| CB442 | 0.01% |
| water | to 100% |
| (pH 7.0 before sterilization). | |

Percentages are by weight, based on the final volume of the medium.

Each of four 2 liter Erlenmeyer flasks, each containing 800 ml of Medium 2 (having the composition specified below), was inoculated with 40 ml of the culture broth from the first flasks, and the flasks were shaken at 28° C. for 96 hours on a rotary shaking machine rotating at a speed of 220 rpm, to give a second seed culture. 1.5 liter of this second seed culture broth was used to inoculate each of two 30 liter jar fermentors each containing 15 liters of Medium 2 (having the composition specified below), which had first been sterilized at 120° C. for 35 minutes and cooled to 28° C. The fermentors were stirred at a speed of 100 rpm at 28° C. for 96 hours with aeration at an air flow of 15 liters per minute.

| Medium 2: | |
|---|---|
| Glucose | 2% |
| Soluble starch | 1% |
| Pressed yeast | 0.9% |
| Meat extract (Kyokuto) | 0.5% |
| Polypeptone | 0.5% |
| NaCl | 0.5% |
| $CaCO_3$ | 0.3% |
| CB442 | 0.01% |
| water | to 100% |
| (pH 7.2 before sterilization). | |

Percentages are by weight, based on the final volume of the medium.

(B) Recovery 3 kg of Celite 545 filter aid (a trade mark for a product of Johns Manville Products Corp.) were added to 30 liters of the whole broth obtained as described above, and the mixture was filtered. The filtrate (29 liters) was passed through a column containing 6 liters of Dowex SBR-P ($Cl^-$) (a trade mark for a product of Dow Chemical). The pH of the eluate was then adjusted to a value of 5.0, after which the solution was passed through a column containing 6 liters of Dowex 50 WX4 ($H^+$) (a trade mark for a product of Dow Chemical). Trehazolin was adsorbed on and thus retained by the column. The column was washed with 20 liters of deionized water and then eluted with 30 liters of 0.5N aqueous ammonia, to give 13 liters of active fractions. The whole of this eluate (13 liters) was concentrated by evaporation under reduced pressure and lyophilized, to give 43.4 g of a crude powder containing trehazolin. The crude powder was dissolved in 2 liters of a 10 mM ammonium formate buffer solution (pH 6.0), and the solution was adsorbed on a column containing 1–5 liters of Dowex 50WX4 (trade mark) which had been previously equilibrated with a 20 mM ammonium formate buffer solution (pH 6.0). The column was washed with 3 liters of the same 20 mM ammonium formate buffer solution, followed by 2 liters of deionized water, after which it was eluted with 0.2N aqueous ammonia. The eluate was fractionated in 500 ml portions. Fractions 2–4, which contained virtually all of the trehazolin, were combined and concentrated by evaporation under reduced pressure. The product was then lyophilized, to give 2.55 g of a crude powder. A crude powder prepared by repeating the steps up to this point was used directly, without any further purification, in Example 3.

This crude powder was adsorbed on a column packed with 200 ml of Avicel (a trade mark for a product of Asahi Chemical Industry Co., Ltd.) using 80% v/v aqueous acetonitrile. The column was washed with 700 ml of 80% v/v aqueous acetonitrile and then eluted first with 500 ml of 75% v/v aqueous acetonitrile, and then with 700 ml of 70% v/v aqueous acetonitrile. The eluate was fractionated in 19 ml portions. Fractions 35–50, containing trehazolin, were combined and concentrated by evaporation under reduced pressure. The residue was then lyophilized, to give 658 mg of a powder. The whole of this powder was dissolved in 150 ml of water, and the pH of the resulting solution was adjusted to a value of 6.0. The solution was then adsorbed on a column packed with 300 ml of Amberlite CG-50 ($H^+:NH_4^+ = 2:3$, trade mark). This column was washed with 500 ml of deionized water and eluted with 0.1N aqueous ammonia. The eluate was fractionated in 20 ml portions. Fractions 92–121, containing trehazolin, were combined and concentrated by evaporation under reduced pressure. The resulting residue was then lyophilized, to give 102.8 mg of a powder. The whole of this powder was dissolved in 10 ml of a 2 mM ammonium formate buffer solution (pH 6.0), and the resulting solution was adsorbed on a column packed with 400 ml of Diaion CHP20P (trade mark for a product of Mitsubishi Kasei Co.), using the same 2 mM ammonium formate buffer solution. The column was eluted with the same 2 mM ammonium formate buffer solution. The eluate was fractionated in 5 ml portions. Fractions 59–73, containing trehazolin, were combined and concentrated by evaporation under reduced pressure. The resulting residue was then lyophilized, to give 18 mg of a powder, which was further purified by elution through Diaion CHP20P, using the same 2 mM ammonium formate buffer solution as the eluent, to give 6.2 mg of a colorless powder.

This powder was purified by preparative thin layer chromatography, as follows. The powder (6.2 mg) was dissolved in a small amount of water and applied to 3 silica gel plates (Merck Art 5715, 20×20 cm). The plates were developed with a 6:1:3 by volume mixture of acetonitrile, acetic acid and water to a height of 15 cm. The band between Rf 0.42 and 0.5 was scratched off from the plates and was packed in a column. The column was eluted with 100 ml of deionized water. The eluate was passed through a column containing 5 ml of Dowex 50WX4 ($H^+$), where the trehazolin was adsorbed and thus retained. The column was washed with deionized water and then eluted with 50 ml of 0.5N aqueous ammonia. The eluate was concentrated by evaporation under reduced pressure, and the resulting residue was lyophilized, to give 5.1 mg of trehazolin as a colorless powder, for which high performance liquid chromatography showed a single peak.

The product had the following properties:

1) Nature and appearance: basic colorless powder;
2) Solubility: soluble in water and methanol, insoluble in acetone and chloroform;
3) Color test: positive to sulfuric acid;
4) Molecular formula: $C_{13}H_{22}N_2O_{10}$;
5) Molecular weight: 366 (determined by FAB-mass spectroscopy—"FAB" is Fast Atom Bombardment);
6) Specific rotation: $[\alpha]_D^{25} + 99.5°$ (c=0.41, $H_2O$);
7) Ultraviolet absorption spectrum: $\lambda_{max}$ nm ($E_{1cm}^{1\%}$), The Ultraviolet absorption spectrum measured in water does not exhibit any characteristic absorption maxima above 220 nm;
8) Infrared absorption spectrum: $\lambda_{max}$ $cm^{-1}$ (in KBr), 3367, 2938, 1663, 1552, 1384 and 1056;
9) $^1$H-Nuclear magnetic resonance spectrum: δ ppm, The $^1$H-Nuclear magnetic resonance spectrum (400 MHz) was measured in deuterium oxide, using TMS (tetramethylsilane) as an external standard, and showed the following signals:
   3.22 (1H, doublet of doublets, J=8.98 and 10.31 Hz);
   3.38 (1H, multiplet, J=2.44, 5.26 and 10.31 Hz);
   3.46 (1H, doublet of doublets, J=8.981 and 9.99 Hz);
   3.53 (1H, doublet, J=11.96 Hz);
   3.55 (1H, doublet of doublets, J=5.26 and 12.21 Hz);
   3.57 (1H, doublet of doublets, J=5.38 and 9.99 Hz);
   3.62 (1H, doublet of doublets, J=2.44 and 12.21 Hz);
   3.63 (1H, doublet, J=11.96 Hz);
   3.77 (1H, doublet, J=4.89 Hz);
   4.02 (1H, doublet of doublets, J=2.08 and 4.89 Hz);
   4.17 (1H, doublet, J=8.55 Hz);
   4.77 (1H, doublet of doublets, J=2.08 and 8.55 Hz);
   5.15 (1H, doublet, J=5.38 Hz);
10) $^{13}$C-Nuclear magnetic resonance spectrum: δ ppm, The $^{13}$C-Nuclear magnetic resonance spectrum (100 MHz) was measured in deuterium oxide, using tetramethylsilane as an external standard, and showed the following signals:
   60.7, 61.9, 69.6, 69.9, 72.0, 73.0, 73.0, 80.1, 80.3, 80.6, 82.8, 87.3 and 161.1;
11) High performance liquid chromatography:
   Column for separation: Senshu Pak ODS-H-2151 (Senshu Scientific Co.), 6φ×150 mm (5μ); Mobile phase: 10% (v/v) acetonitrile-water containing 0.5% of PIC B8 (a product of Waters Inc.);
   Flow rate: 1.5 ml/min;
   Monitored wavelength: Ultraviolet 210 nm;
   A peak having a retention time of 6.9 minutes was observed at a column temperature of 25° C.; and
12) Thin layer chromatography:
   Rf value: 0.44;
   Adsorbent: silica gel on glass plate (Merck Art 5715);
   Developing solvent: a 6:1:3 by volume mixture of acetonitrile, acetic acid and water.

EXAMPLE 2

Preparation of 5-amino-1-(hydroxymethyl)cyclopentane-1,2,3,4-tetraol

A solution of 19.3 mg of trehazolin (prepared as described in Example 1 above) dissolved in 1 ml of 4N aqueous hydrochloric acid was placed in an ampoule and hydrolyzed by heating it at 100° C. for 24 hours. At the end of this time, the reaction mixture was mixed with water and then concentrated to dryness by evaporation under reduced pressure. The residue was again mixed with water and concentrated to dryness by evaporation under reduced pressure, to distill off the hydrochloric acid. The residue from this distillation was dissolved in 20 ml of water, and the pH of the solution was adjusted to a value of 6.0. The resulting solution was passed through a column of 20 ml of Amberlite CG-50 ($NH_4^+$)—trade mark—and the column was washed with 60 ml of deionized water and then eluted with 0.2N aqueous ammonia. The eluate was concentrated by evaporation under reduced pressure, and the residue was lyophilized to give 5.1 mg of impure 5-amino-1-(hydroxymethyl)cyclopentane-1,2,3,4-tetraol as a colorless powder.

The whole of the impure powdery 5-amino-1-(hydroxymethyl)cyclopentane-1,2,3,4-tetraol (5.1 mg) obtained as described above was dissolved in a small amount of water and purified by means of preparative thin layer chromatography, as follows. The solution was applied on two silica gel plates (Merck Art 5715, 20×20 cm) and developed using a 6:1:3 by volume mixture of acetonitrile, acetic acid and water up to a height of 15 cm. The band between Rf 0.36 and 0.47 was scratched off from the plate and packed in a column, which was then eluted with 50 ml of deionized water. The eluate was passed through 10 ml of Amberlite CG-50 ($NH_4^+$) the 5-amino-1-(hydroxymethyl)cyclopentane-1,2,3,4-tetraol being adsorbed on the column. The column was then washed with 50 ml of deionized water and eluted with 50 ml of 0.2N aqueous ammonia. The eluate was concentrated by evaporation under reduced pressure and lyophilized to give 3 mg of the desired 5-amino-1-(hydroxymethyl)cyclopentane-1,2,3,4-tetraol as a colorless powder having the following properties:

1) Color and appearance: basic colorless powder;
2) Solubility: soluble in water, insoluble in acetone and chloroform;
3) Color test: positive to a ninhydrin reaction;
4) Molecular formula: $C_6H_{13}NO_5$;
5) Molecular weight: 179 (determined by FAB-mass spectroscopy);
6) Specific rotation $[\alpha]_D^{25} = -3.7°$ (c=0.51, $H_2O$);
7) Ultraviolet absorption spectrum: $\lambda_{max}$ nm ($E_{1cm}^{1\%}$):
   The ultraviolet absorption spectrum measured in water does not exhibit any characteristic absorption maxima above 210 nm;
8) Infrared absorption spectrum: $\lambda_{max}$ $cm^{-1}$ (in KBr), 3384, 1582, 1474 and 1040;
9) $^1$H-Nuclear magnetic resonance spectrum: δ ppm, The $^1$H-Nuclear magnetic resonance spectrum (400 MHz) was measured in deuterium oxide, using tetramethylsilane as an external standard, and showed the following signals:
   3.12 (1H, doublet, J=7.1 Hz);
   3.56 (1H, doublet, J=11.98 Hz);
   3.62 (1H, doublet, J=12.2 Hz);
   3.62 (1H, doublet, J=6.8 Hz);
   3.78 (1H, doublet of doublets, J=5.5 and 6.8 Hz);
   3.90 (1H, doublet of doublets, J=5.5 and 7.1 Hz);
10) $^{13}$C-Nuclear magnetic resonance spectrum: δ ppm, The $^{13}$C-Nuclear magnetic resonance spectrum (100 MHz) was measured in deuterium oxide, using tetramethylsilane as an external standard, and showed the following signals:
57.8, 61.0, 73.6, 79.4, 81.5 and 81.7; and 11) Thin layer chromatography:
   Rf value: 0.39,
   Adsorbent: silica gel on glass plate (Merck Art 5715),
   Developing solvent: a 6:1:3 by volume mixture of acetonitrile, acetic acid and water.

EXAMPLE 3

Preparation of 2-amino-4-(hydroxymethyl)-3a-5,6,6a-tetrahydro-4H-cyclopent[d]oxazole-4,5,6-triol 100 g of the crude powder prepared as described in Example 1 and containing an estimated 225 mg of trehazolin were dissolved in a mixture of 100 ml of water and 150 ml of 4N aqueous hydrochloric acid, and the pH of the resulting solution was adjusted to a value of 2.5 by the addition of 4N aqueous hydrochloric acid. 8 ml of concentrated hydrochloric acid and 72 ml of water were then added to the solution, to make the total volume 480 ml, and to give a hydrochloric acid concentration of 0.2N. The resulting solution was placed in a round-bottomed flask and then hydrolyzed on an oil bath kept at 100° C. for 6 hours. At the end of this time, the reaction mixture was mixed with water and then concentrated to dryness by evaporation under reduced pressure. The sequence of mixing with water and evaporating to dryness was repeated to distill off the hydrochloric acid. The residue was dissolved in 400 ml of water, and the pH of the solution was adjusted to a pH value of 6.0 by the addition of a 1N aqueous solution of sodium hydroxide. The solution was then diluted with water to a volume of 8 liters. The resulting solution was passed through a column packed with 600 ml of Amberlite CG-50 ($NH_4^+$), and the column was washed with 6 liters of deionized water and then eluted with 0.5N aqueous ammonia. The eluate was concentrated by evaporation under reduced pressure to a volume of 200 ml, and the concentrate was passed through a column packed with 800 ml of Dowex 1X2 ($OH^-$). The column was then eluted with deionized water. After the first 1.5 liters of the eluate had been removed, the subsequent eluate was fractionated in 20 ml portions. Each fraction was assessed by the quantitative analysis described below to determine whether it contained the desired compound. Fractions 70-110, which did contain this compound, were combined and concentrated by evaporation under reduced pressure. The residue was lyophilized to give 30 mg of 2-amino-4-(hydroxymethyl)-3a,5,6,6a-tetrahydro-4H-cyclopent[d]oxazole-4,5,6-triol as a colorless powder having the following properties:

1) Color and appearance: basic colorless powder;
2) Solubility: soluble in water, insoluble in acetone and chloroform;
3) Molecular formula: $C_7H_{12}N_2O_5$;
4) Molecular weight: 204 (determined by FAB-mass spectroscopy);
5) Specific rotation: $[\alpha]_D^{25} + 10.0°$ (c=0.51, $H_2O$);
6) Ultraviolet absorption spectrum: $\lambda_{max}$ nm ($E_{1cm}^{1\%}$), The ultraviolet absorption spectrum measured in water does not exhibit any characteristic absorption maxima above 210 nm;
7) Infrared absorption spectrum: $\nu_{max}$ $cm^{-1}$ (in KBr), 3358, 1668, 1528, 1398 and 1066;
8) 1H-Nuclear magnetic resonance spectrum: δ ppm, The $^1$H-Nuclear magnetic resonance spectrum (500 MHz) was measured in deuterium oxide, using TSP (sodium trimethylsilylpropionate) as an internal standard and showed the following signals:
   3.73 (1H, doublet, J=11.72 Hz);
   3.82 (1H, doublet, J=12.21 Hz);
   3.97 (1H, doublet, J=4.4 Hz);
   4.23 (1H, doublet of doublets, J=4.4 and 2.44 Hz);
   4.37 (1H, doublet, J=8.79 Hz);
   5.03 (1H, doublet of doublets, J=8.79 and 2.44 Hz);
9) High performance liquid chromatography:
   Column for separation: Asahi Pak ES-502C (Asahi Chemical Industry Co., Ltd.);
   Mobile phase: 20 mM ammonium acetate (pH 8.5)+50 mM aqueous sodium chloride;
   Flow rate: 1 ml/min;
   Monitored wavelength: Ultraviolet 210 nm;
   Temperature: 25° C.;
   Retention time: 8.39 minutes.

Quantitative analysis of 2-amino-4-(hydroxymethyl)-3a-5,6,6a-tetrahydro-4H-cyclopent[d]oxazole-4,5,6-triol using Gas Chromatography/Mass Spectrometry The quantitative analysis referred to above was conducted as follows:

A sample was dissolved in a solvent (water) of known liquid volume. 10 μl of the resulting solution were placed in a vial and evaporated to dryness for acetylation. 30 μl of acetic anhydride and 50 μl of pyridine were added to the residue, and the resulting mixture was heated at 60° C. for 40 minutes. Any excess of the reagents was removed by blowing a stream of nitrogen gas through the reaction mixture. The residue was mixed with a known amount of an internal standard (pentaacetyl-1-amino-1-deoxy-β-D-glucose), and the mixture was dissolved in 100 μl of ethyl acetate to make a test sample for gas chromatography/mass spectrometry analysis. The analysis was carried out using a fused silica capillary column (a product of J & W Scientific Co., DB-5, 15 meters) as a gas chromatography column. A test sample (2 μl) was injected, and the column temperature was raised from 60° C. to 280° C. at the rate of 25° C./minute. Negative ions were detected by a chemical ionizing method using methane gas with a quadrupole mass spectrometer Trio-1 (a product of VG). Negative ion peaks at m/z 388 (corresponding to the internal standard pentaacetyl compound) and at m/z 413 [corresponding to the pentaacetate of 2-amino-4-(hydroxymethyl)-3a,5,6,6a-tetrahydro-4H-cyclopent[d]oxazole-4,5,6-triol] were used for quantitative analysis. The content of the 2-amino-4-(hydroxymethyl)-3a,5,6,,6a-tetrahydro-4H-cyclopent[d]oxazole-4,5,6-triol was computed by an internal standard method.

EXAMPLE 4

Preparation of 2-amino-4-(hydroxymethyl)-3a,5,6,6a-tetrahydro-4H-cyclopent[d]oxazole-4,5,6-triol (A) Culture A loop taken from a slant of Amycolatopsis sp. SANK 60791 was used to inoculate each of two 500 ml Erlenmeyer flasks, each fitted with baffle plates and each containing 80 ml of Medium 1 (having the composition given above in Example 1), and the inoculated flasks were incubated at 28° C. for 96 hours on a rotary shaking machine rotating at a speed of 210 rpm to give a seed culture broth.

Two 30 liter jar fermentors each containing 15 liters of Medium 2 (having the composition given above in Example 1) were sterilized at 120° C. for 30 minutes. They were then cooled to 28° C., and 75 ml of the seed culture broth were inoculated into each jar fermentor. The jar fermentors were then stirred at 28° C. at a speed adjusted in the range of from 100 to 400 rpm (in order to maintain 2 ppm of dissolved oxygen) for 144 hours and with aeration at an air flow of 7.5 liters per minute.

(B) Recovery 1.5 kg of Celite 545 filter aid were added to 25 liters of the whole broth [obtained as described in (A) above], and the mixture was filtered to give 23 liters of filtrate. The pH of the filtrate was adjusted to a value of 6.0 by the addition of aqueous hydrochloric acid, and the solution was passed through a column packed with 3 liters of Amberlite IRC-50 ($NH_4^+$) to adsorb the 2-amino-4-(hydroxymethyl)-3a,5,6,6a-tetrahydro-4H-cyclopent[d]oxazole-4,5,6-triol. The column was washed with 15 liters of deionized water and then eluted with 0.5N aqueous ammonia. After the eluate had become alkaline, 4.5 liters of the eluate were collected and concentrated by evaporation under reduced pressure to a volume of 200 ml. The concentrate was passed through a column packed with 450 ml of Dowex 1X2 ($OH^-$) and the column was eluted with deionized water. The first 800 ml of the eluate were removed and the subsequent eluate was fractionated in 20 ml portions. It was determined by quantitative analysis, using either high performance liquid chromatography, as described later, or gas chromatography/mass spectrometry, that fractions 60–90 contained the desired 2-amino-4-(hydroxymethyl)-3a,5,6,6a-tetrahydro-4H-cyclopent[d]oxazole-4,5,6-triol, and so these fractions were combined and concentrated by evaporation under reduced pressure. The concentrate was lyophilized to give 16.6 mg of 2-amino-4-(hydroxymethyl)-3a,5,6,6a-tetrahydro-4H-cyclopent[d]oxazole-4,5,6-triol as a colorless powder having the properties described hereinabove.

Quantitative analysis using high performance liquid chromatography

Column for separation
Asahi pak ES-502C (a product of Asahi Chemical Industry Co., Ltd.);
Mobile phase:
20 mM ammonium acetate (pH 8.5)+50 mM saline;
Flow rate:
1 ml/minute;
Wavelength for detection:
210 nm;
Temperature:
25° C.;
Retention time:
8.39 minutes.

Quantitative analysis using Gas Chromatography/Mass Spectrometry

The quantitative analysis referred to above was conducted using substantially the same procedures as are described in Example 3.

EXAMPLE 5

Preparation of 2-amino-4-(hydroxymethyl)-3a,5,6,6a-tetrahydro-4H-cyclopent[d]oxazole-4,5,6-triol (A) Culture A slant of Micromonospora sp. SANK 62390 was homogenized in 10 ml of a physiological saline solution to make a suspension. 1 ml of the suspension was inoculated into each of two 2 liter Erlenmeyer flasks, each fitted with baffle plates and each containing 500 ml of Medium 3 (having the composition given below), and the inoculated flasks were incubated at 28° C. for 96 hours on a rotary shaking machine rotating at a speed of 210 rpm to make a first seed culture broth.

| Medium 3: | |
|---|---|
| Glucose | 2% |
| Yeast extract (Difco) | 0.5% |
| Polypeptone | 0.5% |
| $CaCO_3$ | 0.1% |
| CB-442 | 0.01% |
| water | to 100% |
| (pH 7.2 before sterilization). | |

Percentages are by weight, based on the final volume of the medium.

30 liters of Medium 3 were placed in a 60 liter jar fermentor and sterilized at 120° C. for 30 minutes. It was then cooled to 28° C., and 600 ml of the first seed culture broth were inoculated into it. The fermentor was stirred at a speed of 165 rpm at 28° C. for 48 hours with aeration at an air flow of 15 liters per minute to make a second seed culture broth.

A 600 liter tank containing 300 liters of Medium 4 (having the composition given below) was sterilized at 120° C. for 35 minutes. It was then cooled to 28° C., and 15 liters of the second seed culture broth were inoculated into it. The tank was then stirred at 28° C. at a speed adjusted in the range of from 82 to 142 rpm (in order to maintain 2 ppm of dissolved oxygen) for 144 hours, with aeration at an air flow of 150 liters per minute and at inner pressure of 0.5 kg/cm².

| Medium 4: | |
|---|---|
| Glucose (previously sterilized at 120° C. for 15 minutes) | 8% |
| Lustergen FK* | 2% |
| Pressed yeast | 1.8% |
| Meat extract (Kyokuto) | 1% |
| Polypeptone | 1% |
| NaCl | 0.5% |
| $CaCO_3$ | 0.3% |
| $K_2HPO_4$ | 0.25% |
| CB-442 | 0.02% |
| water | to 100% |
| pH 7.2 before sterilization. | |

*a trade name for a brand of starch sold by Nichiden Kagaku Co. Ltd.

(B) Recovery 15 kg of Celite 545 filter aid were added to 300 liters of the whole broth prepared as described above, and the mixture was filtered to give 290 liters of a filtrate. The pH of 20 liters of the filtrate was adjusted to a value of 6.0 by the addition of aqueous hydrochloric acid. The resulting solution was passed through a column packed with 3 liters of Amberlite IRC-50 (NH$_4$+) and the desired 2-amino-4-(hydroxymethyl)-3a,5,6,6a-tetrahydro-4H-cyclopent[d]oxazole-4,5,6-triol was held in the column by adsorption. The column was washed with 15 liters of deionized water and eluted with 0.5N aqueous ammonia. After the eluate had become alkaline, 4.5 liters of the eluate were collected and concentrated by evaporation under reduced pressure to a volume of 150 ml. The concentrate was passed through a column packed with 500 ml of Dowex 1X2 (OH$^-$) and eluted with deionized water. The first 1 liter was removed and the subsequent eluate was fractionated in 20 ml portions. Each fraction was examined by the quantitative analysis described in Example 3. Fractions 58-80 were found to contain the active compound, and these fractions were combined and concentrated by evaporation under reduced pressure. The residue was lyophilized to give 9.6 mg of 2-amino-4-(hydroxymethyl)-3a,5,6,6a-tetrahydro-4H-cyclopent[d]-oxazole-4,5,6-triol as a crude powder. The powder was again purified by column chromatography, using a column packed with 100 ml of Dowex 1X2 (OH$^-$) eluted with deionized water, to give 4.8 mg of 2-amino-4-(hydroxymethyl)-3a,5,6,6a-tetrahydro-4H-cyclopent[d]oxazole-4,5,6-triol as a colorless powder having the properties described hereinabove.

EXAMPLE 6

Preparation of 5-amino-1-(hydroxymethyl)cyclopentane-1,2,3,4-tetraol

A solution of 16 mg of powdery 2-amino-4-(hydroxymethyl)-3a,5,6,6a-tetrahydro-4H-cyclopent[d]oxazole-4,5,6-triol dissolved in 2 ml of 6N aqueous hydrochloric acid was sealed in an ampoule and then hydrolyzed by heating at 100° C. for 24 hours. At the end of this time, water was added to the hydrolyzate, and the resulting mixture was concentrated to dryness by evaporation under reduced pressure. The residue was again dissolved in water, and the resulting solution was again concentrated to dryness, to remove the hydrochloric acid, and then the resulting residue was dissolved in 20 ml of water and the pH of the solution was adjusted to a value of 6.0 by the addition of a 1N aqueous solution of sodium hydroxide. The solution was passed through 20 ml of Amberlite CG-50 (NH$_4$+) to hold the 5-amino-1-(hydroxymethyl)cyclopentane-1,2,3,4-tetraol by adsorption, and the column was washed with 60 ml of deionized water and then eluted with a 0.2N aqueous ammonia solution. The eluate was concentrated by evaporation under reduced pressure, to yield 5 ml of a concentrate. This concentrate was placed on a column packed with 50 ml of Dowex 1X2 (OH$^-$), and the column was washed with 200 ml of deionized water and then eluted with 20% v/v aqueous methanol. The eluate was fractionated in 5 ml portions. Fractions 5-23, which exhibited an inhibitory activity against β-glucosidase were combined and concentrated by evaporation under reduced pressure. The concentrate was lyophilized to give 6.2 mg of 5-amino-1-(hydroxymethyl)cyclopentane-1,2,3,4-tetraol as a colorless powder having the properties described hereinabove.

TEST EXAMPLE 1

Biological Activity

Inhibitory activity of 5-amino-1-(hydroxymethyl)cyclopentane-1,2,3,4-tetraol against β-glucosidase Samples of β-glucosidase (separated from almonds), p-nitrophenyl-β-D-glucopyranoside, deoxynojirimycin and castanospermine used in this experiment were all purchased from Sigma Chemicals Co.

The test compounds used were 5-amino-1-(hydroxymethyl)cyclopentane-1,2,3,4-tetraol [compound (I)], and deoxynojirimycin or castanospermine, both of which are known compounds having this type of activity.

A mixture of 0.01 unit/ml of β-glucosidase and 100 μl of a buffer solution (pH 5.6) comprising 20 mM of citric acid, 40 mM of disodium phosphate and the compound under test was allowed to stand at 37° C. for 15 minutes. At the end of this time, 50 μl of a buffer solution containing 3 mg/ml of p-nitrophenyl-β-D-glucopyranoside were added to the mixture, which was then allowed to react at 37° C. for 20 minutes. 20 μl of a 1M glycine/sodium hydroxide buffer solution (pH 10.4) were added to the reaction mixture, and the quantity of p-nitrophenol liberated was monitored by absorbance at 405 nm. Table 7 lists the concentrations β-glucosidase by 50% (IC$_{50}$).

TABLE 7

| Inhibitor | 50% inhibitory concentration of β-glucosidase |
|---|---|
| Compound (I) | 1.0 μg/ml |
| Deoxynojirimycin | 15 μg/ml |
| Castanospermine | 4.3 μg/ml |

TEST EXAMPLE 2

Inhibitory activity of 2-amino-4-(hydroxymethyl)-3a-5,6,6a-tetrahydro-4H-cyclopent[d]oxazole-4,5,6-triol [compound (II)] against rat sucrase According to the method of M. Kessler et al. Biochimica et Biophysica Acta, 506, 136–154(1978)], a brush border membrane enzyme solution of a rat small intestine was prepared from the small intestines of three male rats of the Wistar strain and suspended in 3 ml of physiological saline.

A sample of 4-aminoantipyrine (A 4382) was purchased from Sigma Chemical Co., and samples of peroxidase (Grade I) and glucose oxidase (Grade I) were purchased from Boehringer Mannheim Co. A buffer solution (pH 6.2) comprising 20 mM of citric acid and 40 mM of disodium phosphate was used as the diluent in the following experiment.

Each well of a micro-titer plate with 96 wells (a product of Falcon Co.) was filled with 130 μl in all of a mixture which contained 0.2 mg of bovine serum albumin (Sigma, A 7906), 3 units of glucose oxidase, 0.132 unit of peroxidase, 20 μg of 4-aminoantipyrine, 40 μg of phenol, 3 μ mole of sucrose and a test compound. To the well were added 20 μl of 100-fold diluted solution of a brush border membrane enzyme solution of rat small intestine. The mixture was allowed to react at 37° for 20 minutes and the quantity of glucose liberated was monitored by absorbance at 492 nm.

When the enzyme reactions were conducted without adding a test compound and without adding an enzyme solution, the concentrations of glucose were assumed to be 0% and 100% inhibition, respectively. The concentration of compound (II) required to inhibit the activity of rat sucrase by 50% ($IC_{50}$) was found to be 18 μg/ml.

TEST EXAMPLE 3

Inhibitory activity of trehazolin against silkworm trehalase

Ten silkworm larvae of the fifth instar (total weight 44 g) were homogenized using a Polytrone (trade mark) homogenizer in 120 ml of a buffer solution (pH 5.6) prepared using 20 mM of citric acid and 40 mM of disodium phosphate for 2 minutes, whilst ice-cooling (the same buffer solution was also used hereafter). The homogenized mixture was then centrifuged at a speed of 6,000 rpm for 10 minutes, and the supernatant was separated. 240 ml of acetone were added to 120 ml of the supernatant, whist ice-cooling and stirring, and the resulting mixture was centrifuged at a speed of 9,000 rpm for 20 minutes. The sediment was separated and dissolved in water, and the resulting solution was lyophilized, to give 2.0 g of the crude enzyme.

130 μl of the above buffer solution, 50 μl of a sample solution containing trehazolin at various concentrations and 50 μl of a silkworm enzyme solution prepared as described above and containing 4 mg/ml of the enzyme were placed in a test-tube, and the mixture was shaken on a water bath kept at 37° C. for 15 minutes. At the end of this time, 20 μl of a 250 mM trehalose solution were added, and the mixture was allowed to react for 15 minutes. The reaction mixture was then heated on a boiling water bath for 3 minutes, after which it was cooled with ice-water. It was then centrifuged at a speed of 3,000 rpm for 10 minutes, and the resulting solution, freed from the sediment, was used to determine glucose concentration.

The reaction was conducted using glucose C-test Wako (a product of Wako Pure Chemical Industries Ltd.) and 10-fold quantities of the sample solution over that of the standard procedure. The inhibitory rate was calculated from glucose concentrations attained when using a buffer solution in place of the sample solution and when using a buffer solution instead of the substrate solution as 0% and 100% inhibition, respectively, to compute the concentration needed to inhibit the enzyme activity by 50% ($IC_{50}$), which was found to be 2.0 ng/ml.

We claim:

1. 5-Amino-1-(hydroxymethyl)cyclopentane-1,2,3,4-tetraol and pharmaceutically acceptable salts thereof.

2. 2-Amino-4-hydroxymethyl)-3a,5,6,6a-tetrahydro-4H-cyclopent[d]oxazole-4,5,6-triol and pharmaceutically acceptable salts thereof.

* * * * *

UNITED STATES PATENT AND TRADEMARK OFFICE
CERTIFICATE OF CORRECTION

PATENT NO. : 5,260,447
DATED : November 9, 1993
INVENTOR(S) : NAKAJIMA et al

It is certified that error appears in the above-identified patent and that said Letters Patent is hereby corrected as shown below:

Title page, left column, under [22], insert

--[30]  Foreign Application Priority Data

```
Feb. 15, 1991  [JP]  Japan .....  3-21976
June  4, 1991  [JP]  Japan .....  3-132946
Aug. 26, 1991  [JP]  Japan .....  3-213450
Oct. 21, 1991  [JP]  Japan .....  3-272412--
```

Signed and Sealed this

Twenty-first Day of March, 1995

Attest:

BRUCE LEHMAN

Attesting Officer       Commissioner of Patents and Trademarks